(12) United States Patent
Staggs

(10) Patent No.: US 11,766,250 B1
(45) Date of Patent: Sep. 26, 2023

(54) WOUND ANCHOR STERILE PEN

(71) Applicant: GRAM TACTICAL LLC, Nashville, TN (US)

(72) Inventor: James William Staggs, Nashville, TN (US)

(73) Assignee: GRAM TACTICAL LLC, Nashville, TN (US)

(*) Notice: Subject to any disclaimer, the term of this patent is extended or adjusted under 35 U.S.C. 154(b) by 922 days.

(21) Appl. No.: 16/296,064

(22) Filed: Mar. 7, 2019

Related U.S. Application Data

(60) Provisional application No. 62/686,955, filed on Jun. 19, 2018, provisional application No. 62/639,736, filed on Mar. 7, 2018.

(51) Int. Cl.
| | | |
|---|---|---|
| *A61B 17/00* | (2006.01) | |
| *A61B 17/04* | (2006.01) | |
| *A61B 17/12* | (2006.01) | |
| *A61L 31/04* | (2006.01) | |

(52) U.S. Cl.
CPC ........ *A61B 17/0057* (2013.01); *A61B 17/0401* (2013.01); *A61B 17/1204* (2013.01); *A61B 2017/0409* (2013.01); *A61L 31/044* (2013.01)

(58) Field of Classification Search
CPC ............ A61B 17/0057; A61B 17/0401; A61B 2017/00623; A61B 2017/00637; A61B 2017/00641; A61B 2017/00654; A61B 2017/00676; A61B 2017/1205; A61B 2017/0409; A61B 2017/00898
See application file for complete search history.

(56) References Cited

U.S. PATENT DOCUMENTS

| | | | | |
|---|---|---|---|---|
| 5,571,181 | A * | 11/1996 | Li ...................... | A61L 31/148 604/311 |
| 7,373,939 | B1 * | 5/2008 | DuBois et al. ..... | A61M 16/0472 128/200.26 |
| 8,932,328 | B2 * | 1/2015 | Megaro et al. ... | A61B 17/06166 606/228 |
| 2007/0129758 | A1 * | 6/2007 | Saadat .............. | A61B 18/1442 606/232 |
| 2010/0114156 | A1 * | 5/2010 | Mehl ................. | A61B 17/0057 606/213 |
| 2016/0015376 | A1 * | 1/2016 | Riina et al. ........ | A61B 17/0401 606/144 |

OTHER PUBLICATIONS

Skin The History Guide https://www.histology.leeds.ac.uk/skin/skin_layers.php#:~:text=Skin functions and Layers,-Some facts about&text=The thickness of skin varies, and outside of your body!*

* cited by examiner

*Primary Examiner* — Sarah A Simpson

(57) ABSTRACT

A wound anchor sterile pen (WASP), and a system and method for administering to wounds of mass casualties using multiple WASPs. This system has tactical, EMS, Mass Casualty, disaster, lay-responder and self-use in mind. It is also designed to allow tracking using RFID tags and Blockchain technology. It is a needed product for treating mass casualties in combat as well as in shooting situations such as those that have recently occurred at schools, night clubs and other large gatherings. The device can assist in stopping blood flow from wounds and give the injured person more time to obtain hospital treatment to hopefully preserve the person's life.

14 Claims, 12 Drawing Sheets

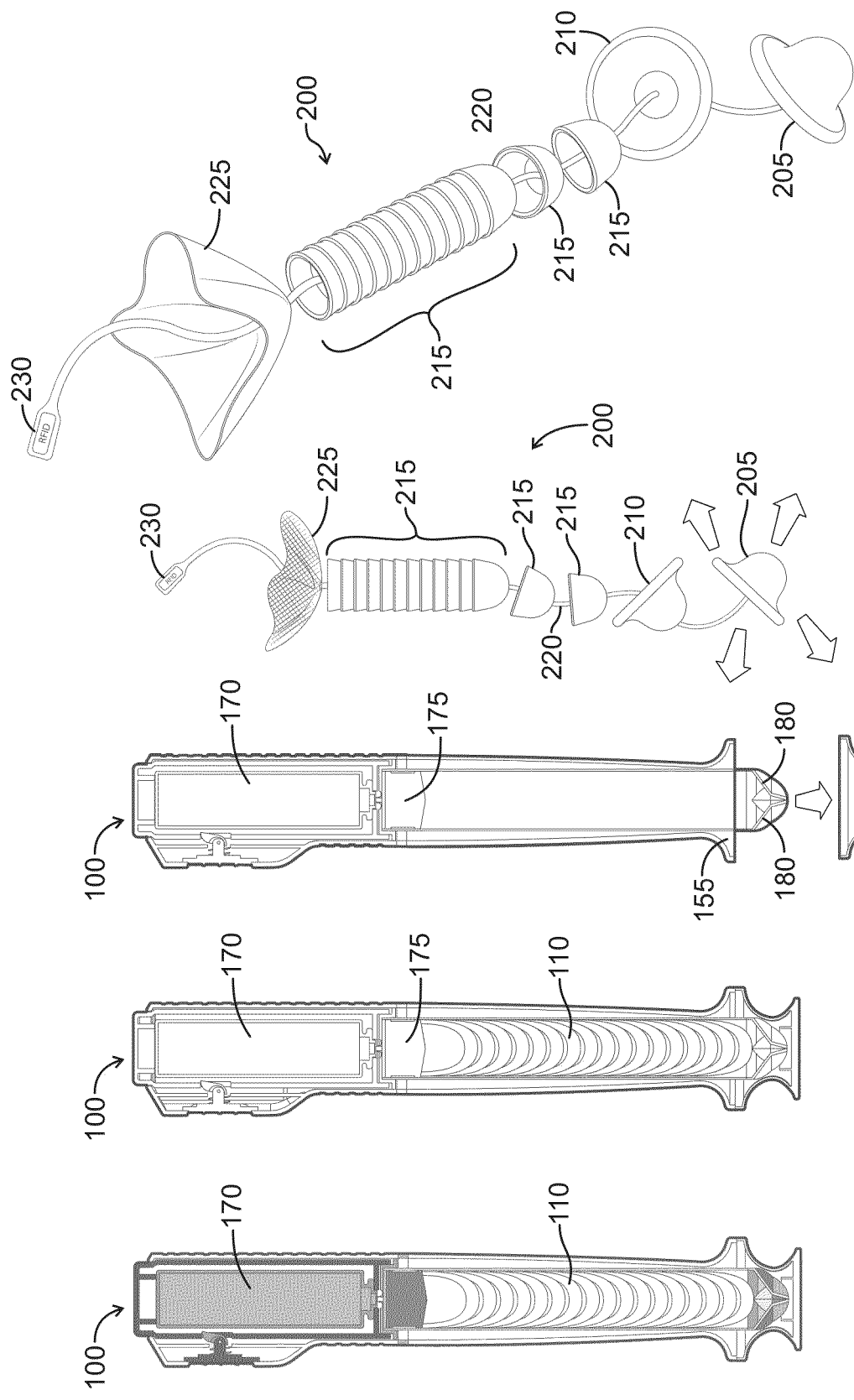

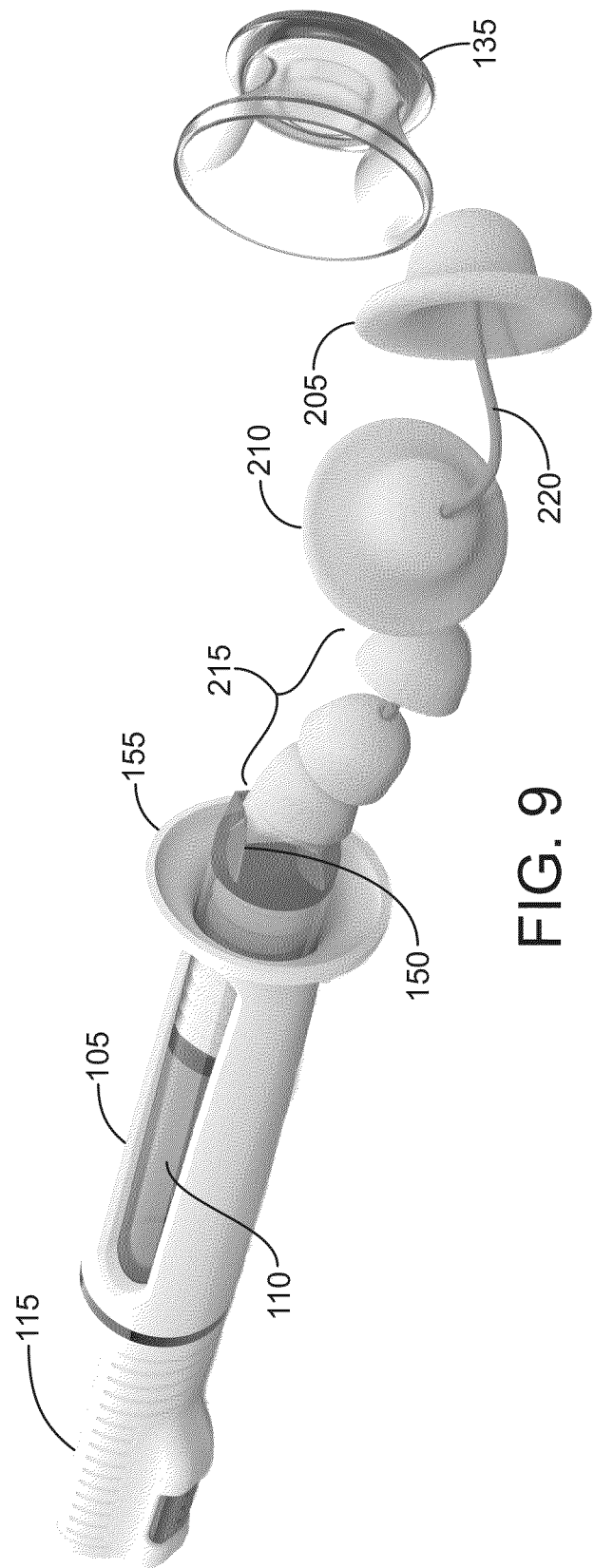

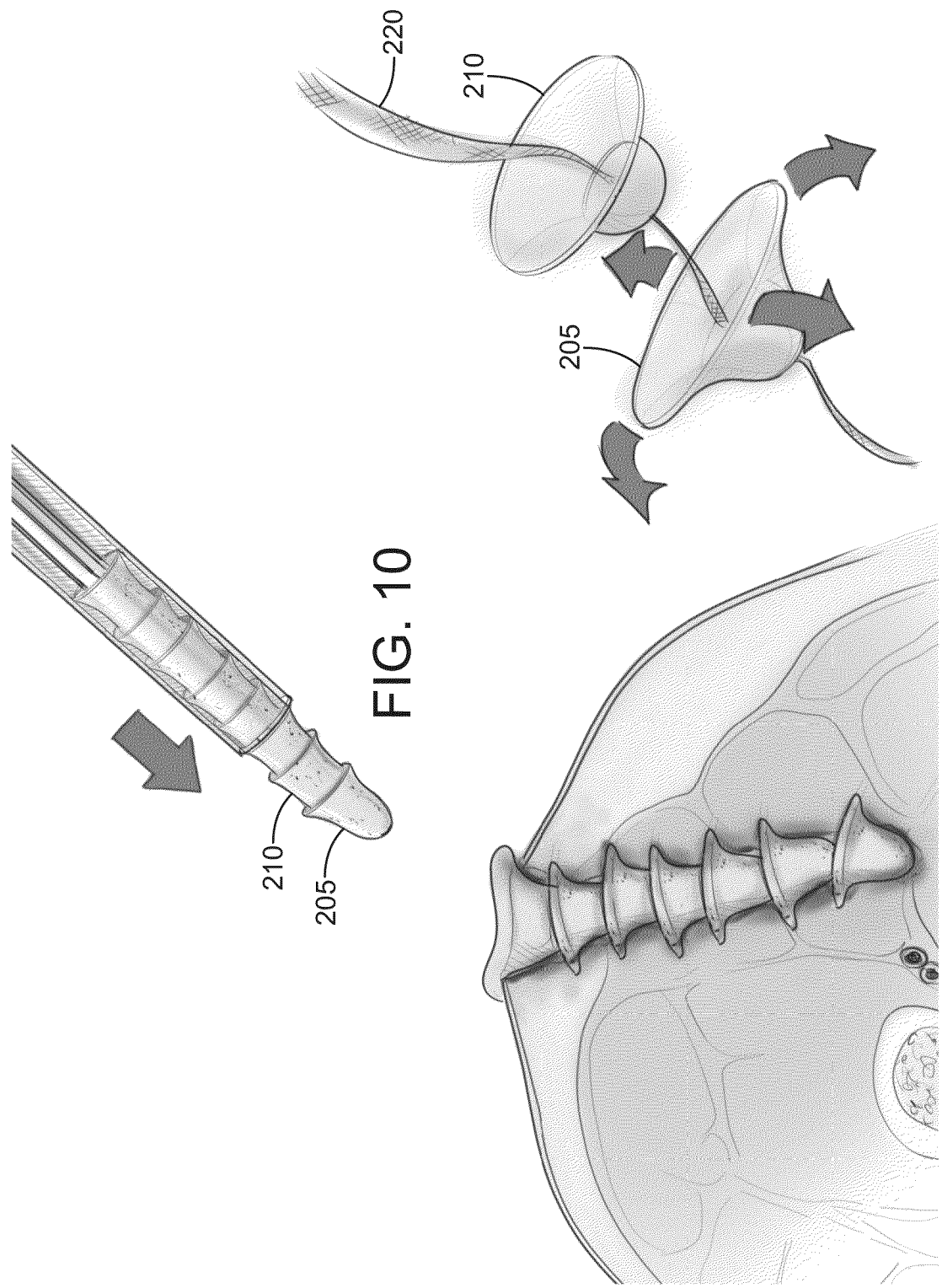

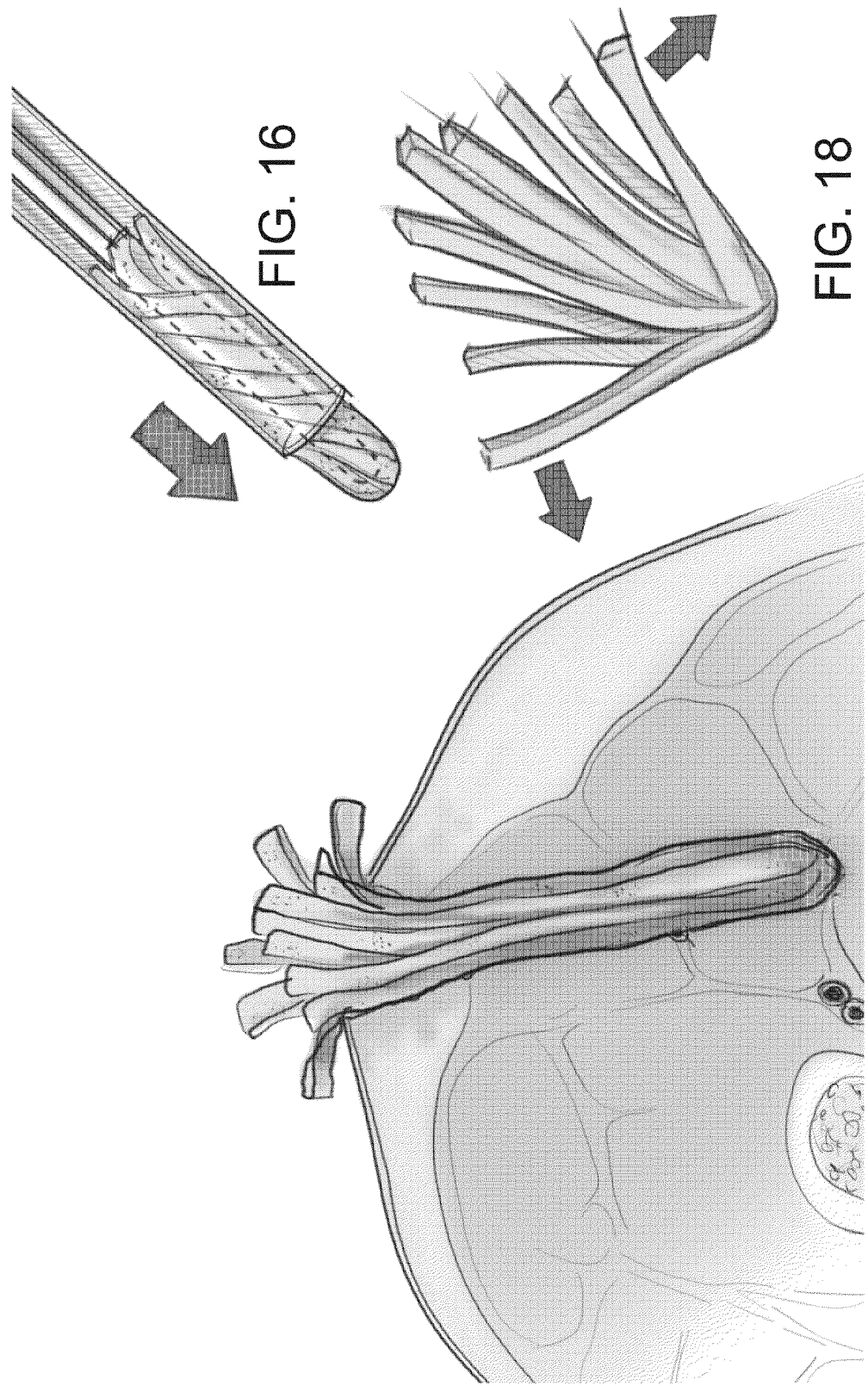

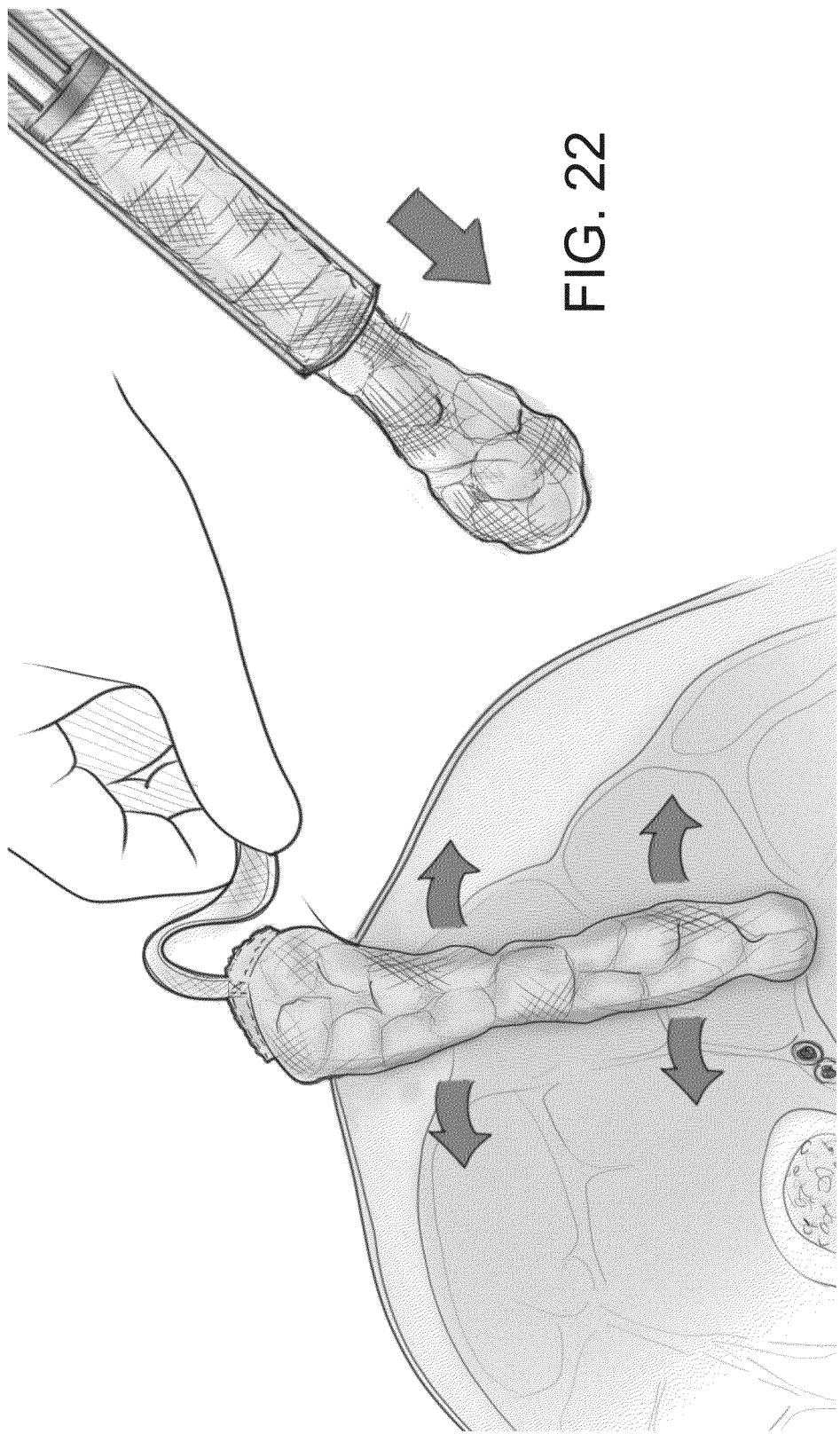

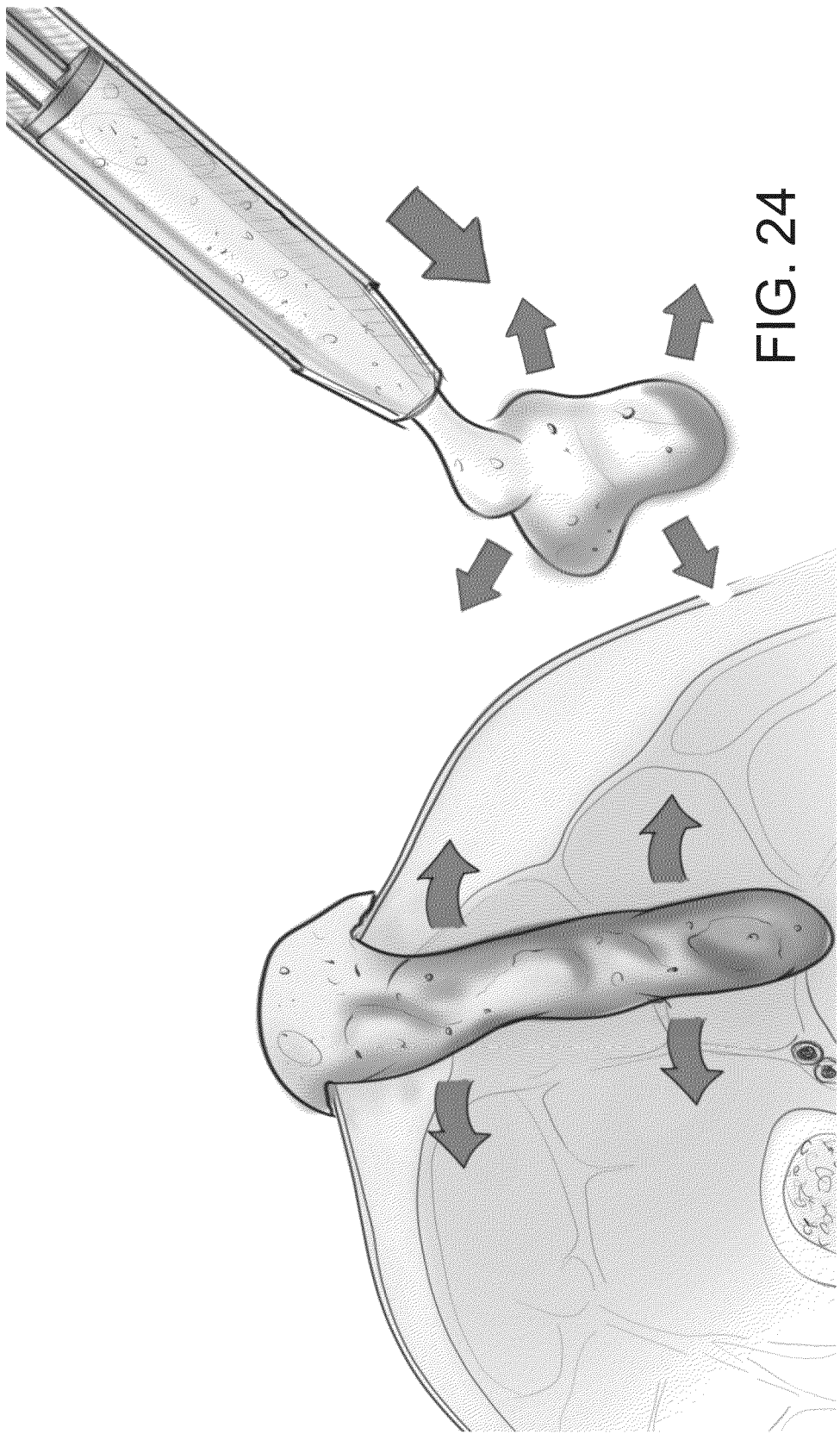

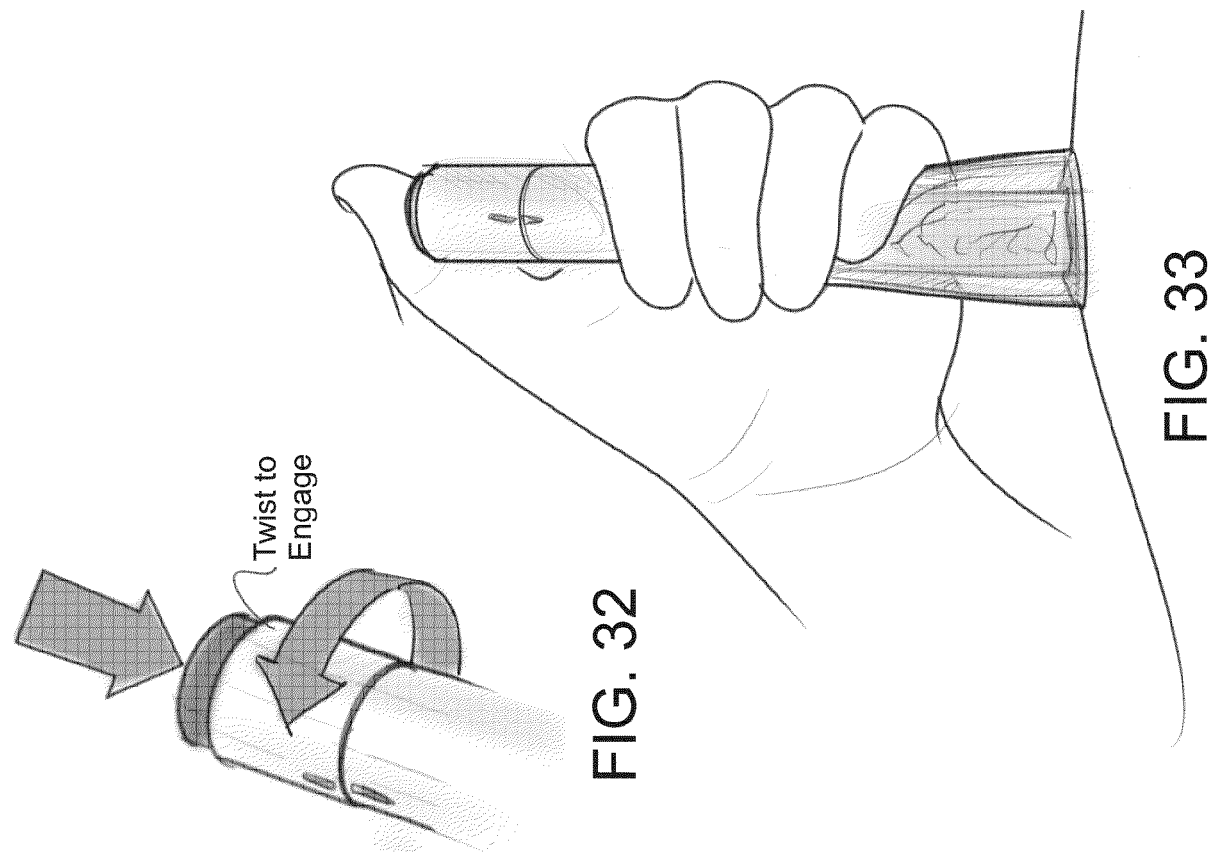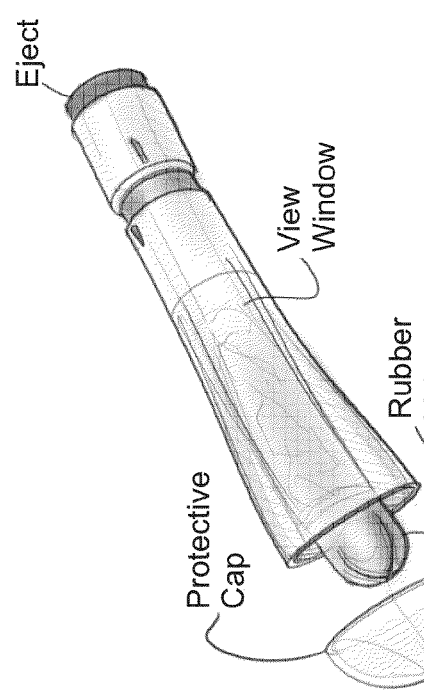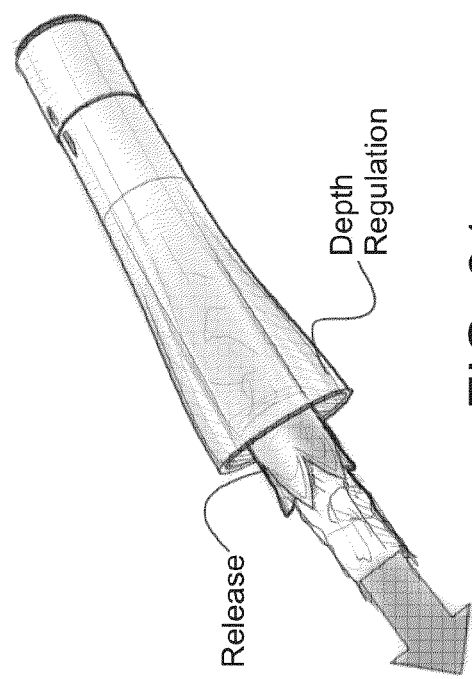

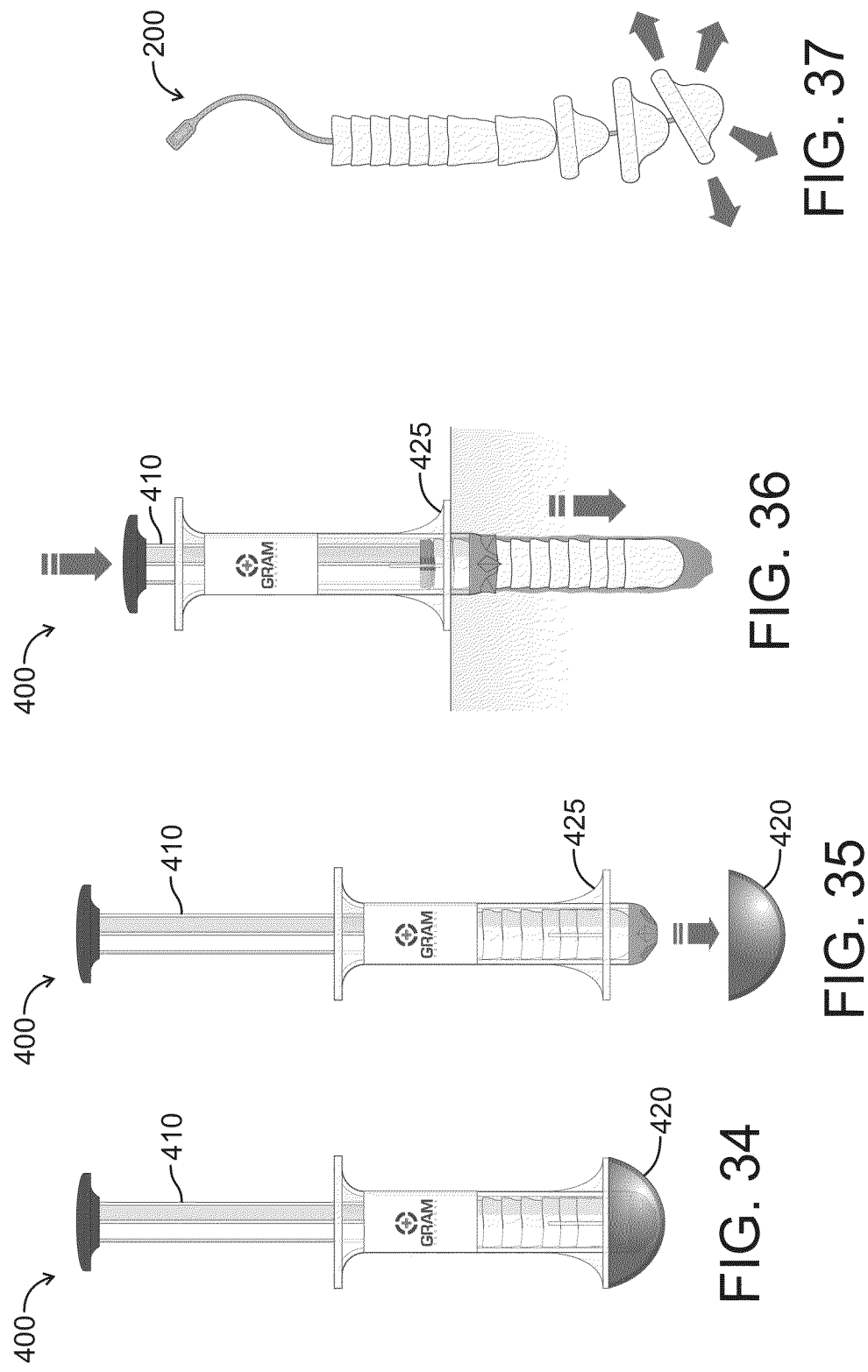

WOUND ANCHOR STERILE PEN

CROSS-REFERENCE TO RELATED APPLICATIONS

This application claims the benefit of U.S. Provisional Pat. Applications Nos. 62/686,955 filed Jun. 19, 2018 and 62/639,736 filed Mar. 7, 2018, the entire content of each of which is expressly incorporated herein by reference thereto.

BACKGROUND

Exsanguination is a leading cause of early death following a traumatic injury. Depending upon the age, health, and fitness level of the individual, people can die from losing half to two-thirds of their blood; a loss of roughly one-third of the blood volume is considered very serious. Even a single deep cut can warrant suturing and hospitalization, especially if a vein or artery is severed or damaged. Protocol-driven transfusion strategies are often used to replace lost blood and improve patient survival, reduce hospital stays and reduce patient care costs. On a battlefield or other locations where prompt receipt of blood plasma is not possible, however, there is a need to prevent or reduce exsanguination until the injured person can obtain appropriate medical treatment. Bandages and tourniquets have been used to prevent loss of blood until the person can obtain medical treatment, but these devices are not satisfactory for all situations. In particular, deep wounds from weapon fire, knives, shrapnel or other sources can be inflicted on just about any part of the person's body, and in areas where use of such devices is not possible or where they are not effective.

One way to try to prevent blood loss is to block or fill the wound with a blood absorbing material. This can reduce bleeding to but time for the injured person to be transported to a medical facility. In this regard, U.S. Pat. No. 5,571,181 discloses a soft tissue closure system for closing tissue voids using a syringe type delivery device and a self-expandable, resort bubble implant disposed with in the delivery device in a compressed configuration. After release of the implant member into a soft tissue void, the implant member self-expands to conform to the shape of the void to seal it.

Also, Chinese Patent Application CN 206424114U discloses a medical hemostatic pen, comprising, a piercing mechanism, an air guide plate and a second pen beneath a first pen. The first pen is fixedly connected with a second pen, with the bottom surface of the interior of the first pen provided with the piercing mechanism that includes a puncture needle. The second pen has a hollow cavity and the air guide plate and a piston are provided in the cavity. A chamber located below the piston chamber is filled with a plurality of hemostatic members, and the air guide plate is operatively associated with a high-pressure gas cylinder in order to dispense the hemostatic members into a gunshot or similar wound to stop bleeding.

There still remains a need, however, for new and more efficient wound treatment devices and methods, and these are now provided by the present invention.

SUMMARY OF THE INVENTION

The present invention relates to a wound anchor sterile pen (WASP), and a system and method for administering to wounds of mass casualties using multiple WASPs. This system has tactical, EMS, Mass Casualty, disaster, lay-responder and self-use in mind. It is also designed to allow tracking using RFID tags and Blockchain technology. It is a needed product for treating mass casualties in combat as well as in shooting situations such as those that have recently occurred at schools, night clubs and other large gatherings. The device can assist in stopping blood flow from wounds and give the injured person more time to obtain hospital treatment to hopefully preserve the person's life.

In particular, the invention provides a device for delivering anchors into a person's wound to stop bleeding therefrom. The device comprises a body that has a lower section having an interior portion that stores at least one and preferably a plurality of compressed anchors made of blood absorbing material that expands in size initially after leaving the body and further upon contacting and absorbing blood and an upper section having an interior portion that is configured to contain an anchor deployment component configured to deploy the anchors from the lower section. The body also includes a forward end including a knife blade, and a depth limiter, wherein the knife blade is configured to cut through a skin surface to facilitate introduction of the tip and deployment of the anchors; and the depth delimiter is configured to control insertion depth of the device into a person's wound.

In this device, the forward end may include a tip and a neck connecting the tip and the lower section, wherein the tip is configured to close off the interior portion of the lower section, the tip includes a plurality of slits through which the anchor(s) pass when deployed with the slits configured to separate the anchors during multiple anchor deployment. In this arrangement, the knife blade would be positioned on the neck and preferably has a length between 1 and 4 mm. Also, the depth delimiter is part of the lower section and is the widest portion of the lower section with a width that is also larger than that of the forward end.

In one embodiment, the anchor deployment component is a replaceable cartridge that contains carbon dioxide and a piston that is moved to deploy the anchors when carbon dioxide is released from the cartridge. In this embodiment, the pen body further comprises a trigger button configured to deploy one or more anchors from the interior portion of the lower section through the forward end by releasing carbon dioxide from the cartridge; and a safety switch on the pen body configured to prevent the trigger button from deploying the one or more anchors until desired.

The one or more anchors are typically stored in the interior portion of the lower section of the device, wherein the anchors have a first size while being stored in the interior portion of the lower section and a second size after being deployed from the device, with the second size being larger than the first size and resulting from initial expansion of the compressed anchors after deployment from the interior portion of the lower section. When multiple anchors are provided, they are joined together by a tether penetrating through each of the anchors, with the anchors made of cotton, polymers, or a combination thereof and optionally including hemostatic agents, antibiotics, medicines, or a combination thereof. This allows the deployed anchors to be more easily removed from the wound, e.g., when the person is being provided with further medical treatment.

In another embodiment, the anchor deployment component is a plunger that is movable within the tube to deploy the anchors through the forward end of the device. This is a simpler, lower cost device that still is very effective for treating wounds to reduce or prevent exsanguination.

The invention also provides a cartridge for a device that delivers anchors into a person's wound to stop bleeding therefrom. This cartridge comprises a plurality of anchors made of blood absorbing material that expand in size initially after leaving the body and further upon contacting and absorbing blood; and a tether penetrating through and connecting each of the anchors together, the tether secured to the anchor that is first to be deployed from the cartridge. The cartridge can also include a fabric dressing following the anchor that is last to be deployed from the cartridge to help close off the wound, and a RFID tag attached to tether behind the fabric dressing so that the use and location of the device can be easily determined.

For convenience in handling the device, the upper section preferably includes multiple non-slip rubber grips. For sterility, the device may include a removable cap to cover the forward end. Windows are provided to view the anchor cartridge contents so that the user is aware that there are sufficient anchors available for deployment.

The plurality of anchors preferably include a first anchor that has a size larger than the remaining anchors or first and second anchors that each have has a size larger than the remaining anchors, with each anchor made of cotton, polymers, or a combination thereof and optionally including hemostatic agents, antibiotics, medicines, or a combination thereof. The anchors are flexible preferably with a bell shape and the tether is a cord or line made of metal or high tensile plastic or fiber material.

The invention also relates to a method for treating wounded people in a mass casualty situation, which comprises deploying one or more anchors from a device disclosed herein directly into a wound. The anchors expand upon deployment from the device from their compressed configuration therein. After being placed in the wound, the anchors expand further when contacting blood from the wound. The expanded anchors thus apply pressure to interior portions of the wound to reduce or stop blood flow. Preferably, the anchors expand to at least double their size after deployment from the device and contacting blood. The pressure that is exerted is done in a hands free manner so that the person deploying the anchors can then move on to assist other wounded persons.

BRIEF DESCRIPTION OF THE DRAWINGS

Preferred features of the invention are illustrated by the appended drawing figures, wherein:

FIGS. 4, 5 and 6 are side, cross-sectional views of the device of FIG. 1 to illustrate the arrangement and compression of the anchors in the cartridge;

FIGS. 7 and 8 are side and perspective views, respectively, for the tethered anchors of the device of FIG. 1;

FIG. 9 is a perspective view of the device with the anchors partially deployed;

FIG. 10 is an expanded view of the anchors being deployed from the device;

FIG. 11 is a view of the anchors deployed into a wound;

FIG. 12 is an expanded view of the anchors and tethers to illustrate how they expand after being deployed and before entering the wound;

FIG. 16 is a view of a different configuration anchor as it is emerging from the device;

FIG. 17 is a view of the anchor of FIG. 16 placed in a wound;

FIG. 18 is a view of the anchor expanding after it has been deployed;

FIG. 22 is a view of another anchor being deployed from the device;

FIG. 23 is a view of the anchor of FIG. 22 deployed into a wound and to show the tether that can be used for later removal of the anchor from the wound;

FIG. 24 is a view of a semisolid anchor being deployed from the device;

FIG. 25 is a view of the anchor of FIG. 24 deployed into a wound;

FIGS. 30-33 are views of a gas cartridge powered device and a twist mechanism that is used to engage and activate the device;

FIGS. 34-35 are side views of a manual piston syringe device for deploying anchors;

FIG. 36 is a side view of the device of FIGS. 34-35 showing the anchors that are deployed into a wound; and FIG. 37 is a perspective view of the tethered anchors for the device of FIGS. 34-36.

DETAILED DESCRIPTION OF THE INVENTION

In combat or in situations involving shootings, bombings or terrorist attacks, mass casualties occur and the injured that receive prompt medical attention have the best chance for survival. In such situations, it is dangerous for medical personnel to reach the injured and of course, the environment where the casualties are located are not appropriate for conducting quality care.

In these situations, blood loss from injured persons becomes a major factor as to whether the person will survive. The invention now provides a compact, pen-like device that contains a plurality of anchors for deployment into the wound either by manually, gas powered or spring powered deployment assistance so that wounds can be filled with one or more of the anchors in an attempt to reduce or preferably stop bleeding. As noted, this then provides time for the injured person to hopefully be transported to a medical care facility for quality treatment.

Figure 1:
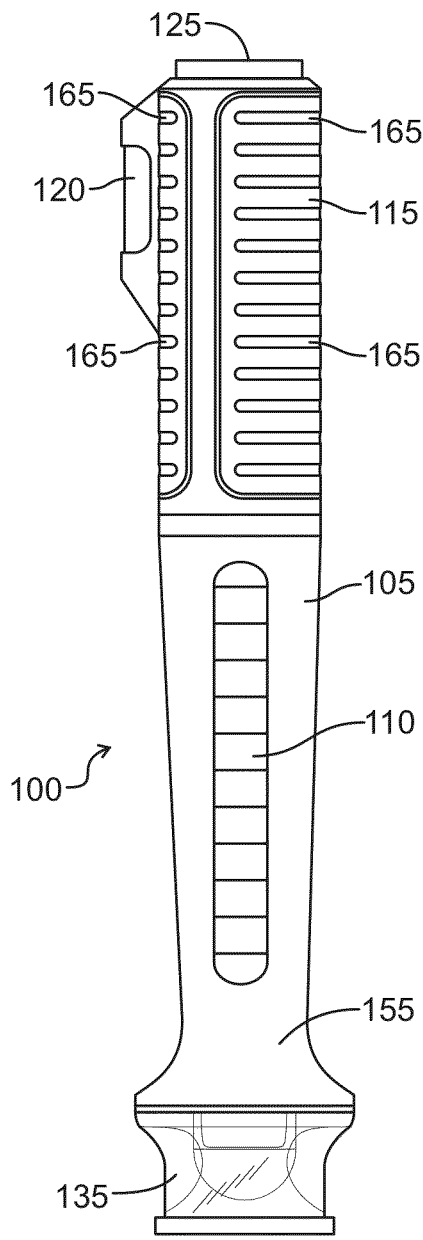
FIG. 1 is a side view of a WASP pen device for delivering cup shaped sterile, stacked and expandable anchors into a wound.
Figure 2:
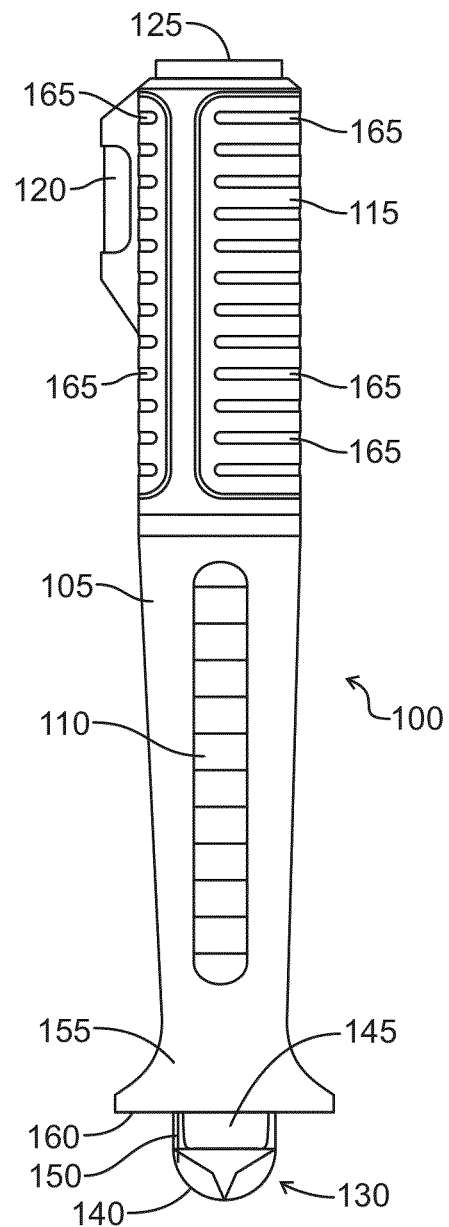
FIG. 2 is a side view of the device of FIG. 1 with the end cap removed.
Figure 3:
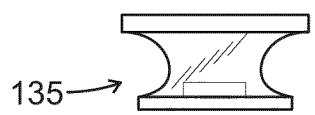
FIG. 3 is a side view of the end cap of the device of FIG. 1.

FIGS. 1-6 illustrate a WASP device 100 for delivering cup shaped sterile, stacked and expandable anchors that are to be placed into a wound. FIG. 1 is a perspective view of device 100 while FIG. 2 illustrates the device 100 with the end cap removed. The end cap is shown in FIG. 3. The device is preferably configured in the shape and size of a pen. Wound anchors 110 are stacked and nested in series in the pen body 105. The anchors are visible through a large viewing window. The shape of these anchors will be such that they will nest in series with enough strength and flexibility to be inserted into wounds by deployment of a source of energy inside the upper end 115 of the pen body. Typical energy sources are a coil spring or gas actuation from a carbon dioxide cartridge. A safety switch 120 is engageable to activate the device and the anchors are deployed by pressing a trigger button 125.

Energy sources of these types are well known in the art and are similar to those used in needless and short needle medicament injectors. As general examples, the energy sources of the devices disclosed in the following documents can be used: U.S. Pat. Publication 2005/0192530, which is a needle-less injector that includes a reservoir or ampoule that contains a quantity of a fluid to administer single or multiple injections in series, to multiple recipients without need for refilling, with the injector powered by a spring, by gas pressure or by electricity; (2) U.S. Pat. Publication 2015/0202369, that discloses an injection device for a spring driven injection of a liquid drug by action upon a cartridge containing the drug using mechanical components that make up the dose setting and injection mechanism, which is a torsion spring in which a torque is stored with very limited axial compression; and (3) U.S. Pat. 6,648,850 which provides a jet injection device comprising a body having a cylinder bore in which an injection piston is movable to cooperatively define a variable-volume chamber for holding a dose of liquid medication, and a power source for forcefully moving the piston in response to communication of gas pressure to a gas pressure piston, with a trigger assembly provided for effecting communication of pressurized gas to the gas pressure piston. Each of these devices are incorporated herein by reference for their disclosure of various energy sources that operate on a piston to deliver the medicament. In the present invention, the same type of operation is use except that the piston contacts the stacked and nested anchors to deliver them from the forward end 130 of the device.

A preferred device uses a carbon dioxide cartridge as the power source. The gas-powered device will regulate the pressure and have a peep valve or similar to prevent over pressure. The gas-powered device can be depressed and repeated multiple times if desired. This prevents a "one shot wonder" and will allow for controlled delivery. This multiple use feature can also make the anchor cartridges reloadable, exchangeable or used to power other devices. For example, a cartridge can be designed to deliver a medicament or other chemicals.

When not in use the forward end 130 of the device is protected by the removable end cap 135. This end cap which must be removed prior to use is typically made of a clear plastic and keeps the anchors sterile. The end cap 135 can be easily removed using only one hand to facilitate operation of the device 100 to deploy the anchors. The forward end of the device includes a tip 140 that closes off the interior portion of the body but that includes slits that separate to allow dispensing and deployment of the anchors when the device is activated. The forward end of the device also includes a neck 145 that includes a knife blade 150 that can be used to assist cut the skin around a wound opening to facilitate introduction of the tip and deployment of the anchors. The knife blade would be relatively small, sticking out from the neck on one or two sides for about 1 mm at the forwardmost end to about 3 or 4 mm toward the rearward portion of the neck. The forward end 130 of the device (tip 140 and neck 145) act as a delivery nozzle which is long enough to insert the anchors just below the wound line at the correct depth. It helps find, stabilize and center itself in the wound. This assists in one-handed and blind delivery. Centering is important in order to find the correct trajectory of the wound before insertion of anchors. The distal gasket keeps the anchor column sterile allowing for easy insertion through it.

The forward end of the body includes a depth limiter 155. This allows for the device to be placed at correct depth for deployment. It also impairs the device from being inserted too deep into the wound and aids in the one-handed or blind delivery of the anchors. The depth limiter has a forward cone 160 that contact's the person's skin around the wound in order to properly locate the tip 140 in the upper part of the wound for deployment of the anchors. To assist in operating the device, the upper end 115 of the body includes multiple non-slip rubber or polymeric portions 165 to facilitate secure gripping of the device. The materials for these portions would be the same as those used on toothbrushes to facilitate gripping when the material is wet due to water or even from blood. The device itself will be made of mil-spec polymers and or similar materials. It can be made of metal with the polymeric gripping portions included. It is easy to grip when wet and can be easily operated with one hand and even with a glove on that hand. The device is useful in all conditions and environments and can be used from any angle.

FIGS. 4-5 are cross-sectional views to illustrate the nested anchors before (FIG. 4) and during (FIG. 5) activation of the device. FIGS. 5-7 show a carbon dioxide cartridge 170 that is activated to move the piston and deploy the anchors. The safety switch 120 must be disengaged before the trigger 125 will deploy the column of nested anchors. FIG. 6 best illustrates the slits 180 on the forward tip which are visible after the end cap is removed. FIG. 6 also shows the device after the anchors are fully deployed. At that point, the forward end 105 of the body, which is configured as a removable cartridge, can be removed and a new cartridge of anchors added so that an additional injured person can be treated. This would be for devices that have a sufficient energy source to allow multiple deployments. Of course, in a mass casualty event it may be better to simply provide multiple devices that each provide a single use so that no time is lost finding and replacing anchor cartridges. When used in a medical office setting, however, the cartridge can be replaced. The cartridge can include a new end cap or the cap from the prior device can be reused instead.

FIGS. 7-9 illustrate the preferred anchors 200 for use in the present device. The lead anchor 205 as well as a second 210 or even a third anchor are configured with an enlarged shape such as the bell shape that is shown, so that they can be injected into the wound to provide forward and lateral pressure to stop bleeding. For deep wounds a number of additional, slightly smaller cup shaped anchors 215 follow the lead anchors to fill in the remaining opening of the wound. All of the anchors are connected by a tether which runs throughout the entire anchor stack to the first anchor where it is securely attached thereto. The tether is preferably a cord or line of metal or high tensile plastic or fiber material.

The anchors are nested in a way that provides stability on insertion and handle almost any depth wound if scaled properly. The anchors are also flexible enough to better adapt to non-linear wound track. Stacking of multiple small anchors allows for the device to penetrate to required depth. For example, if a 3-inch column was composed of 15 small anchors and the wound was 2 inches deep. Approximately 10 anchors would be inserted and the other 5 would remain on the exterior. The exterior 5 anchors would be cinched down under the one-way dressing providing more pressure on the exterior. The anchors can be scaled almost any diameter. The scalability of this product allows these anchors to be used in varying wound geometries. The preferred shape of the anchor generally represents an arcuate cup or bell although as noted herein other shapes and designs can be used.

The anchor shape is designed to change form in two ways. A slight force is applied opposite to the insertion force by the tether upon removal of the device after injection. This force pulls the center mass of the anchor proximal and pushes the edges of the cup outwards. This radial expansion effectively increases the circumference of the anchor becoming more the twice the diameter of insertion size. Secondly the anchor material expands when absorbing blood such that it expands to many times its original size when contacting blood, and as much as 10 to 15 times or more.

The anchors will be made of a soft, flexible expandable material. The material will have enough structure, strength, and flexibility to be inserted into the wound safely and many different wound geometries. It is also made of a bio-inert material that expands to many times its size when encountering blood or bloody bodily fluids. It can also be made in a geometry or of a material that will change shape when an external force is applied. It can be made of any combinations of these properties or materials to meet any of these descriptions and needs.

A preferred material for the anchors is similar to materials used to absorb blood such as menstrual blood. For example, the anchors can be made simply of cotton gauze that is capable of absorbing blood. These type materials are the principal dressings currently in use by the armed forces and by civilian trauma units for external hemorrhage. For even better performance, other types of absorbent fibers, fabric or foams can be used.

One blood absorbent material is disclosed in U.S. Pat. 5,772,645, and is made of layers of hydrophilic fibrous materials such as hydrophilic fibers of rayon or cotton. Small recesses can be formed by embossing the absorbent layer or by using needles to provide a density of 0.4 to 0.6 g/cm$^3$ and small openings or cavities that assist in absorbing blood.

Yet another suitable material for the anchors is a polymeric absorbent foam such as is disclosed in U.S. Pat. 5,845,809. These foams provide a substantially open-celled foam structure with intercellular openings, holes or "windows" that provide passageways large enough to permit free and ready movement of blood and blood based fluids from one cell to another within the foam structure for effective absorption. In addition to being open-celled, these polymeric foams are rendered sufficiently hydrophilic to permit the foam to absorb blood and blood-based fluids. The internal surfaces of the foam structures are rendered hydrophilic by residual hydrophilizing surfactants left in the foam structure after polymerization, or by selected post-polymerization foam treatment procedures that are described in that patent.

The anchor material can be combined with hemostatic agents, antibiotics, medicines, and other materials. This will prevent injury, assist in hemostasis, administer medication, apply pressure, prevent infection, pain management and many other medical or practical reasons. For example, it is also possible to use materials that initiate or accelerate blood clotting as disclosed in U.S. Pat. 5,800,371. That patent discloses a hemostatic wound dressing material that contains a mixture of superabsorbent polymer and microfibrillar collagen to provide rapid intervention of exsanguination more effectively than cotton gauze. As a mixture of particles, the combination of these two materials efficiently initiates clotting and arrests hemorrhaging, while promoting rapid clot propagation in a direction opposing that of the blood flow.

In the device, the anchors are slightly compressed to conserve space in the device and to more importantly enable the deployed anchors to exert sufficient pressure on the wound to slow down and stop blood flow or exsanguination. These anchors both expand upon delivery from their compressed state and then expand further upon contact with blood or bloody body fluids. The combination of the shape change and expansion both anchor and expand to apply pressure in all directions in the wound. This shape change also applies an added physical force outward pressure which will become greater than what is achievable from the expandable anchors alone. This is generally sufficient to achieve hemostasis.

The anchors that are used in the present invention are designed to provide maximum expansion so that wounds or tissue voids of different sizes can be rapidly filled, blocked or sealed. First of all, the anchors are sufficiently flexible so that they can be compressed into the reservoir or cartridge of the pen device. Typically, the anchors are compressed by the cartridge or housing by at least 20 to as much as 60% of their initial, uncompressed volume. This way, as the anchors are being deployed, they begin to expand even as they are entering the wound. After the necessary number of anchors are placed in the wound, they then absorb blood to further expand. This can cause the anchors to grow by at least another 10 to 25% in size, thus providing a very effective blocking of all wound openings. This combination of the different shapes disclosed herein along with the dual expansion properties is highly effective in closing wounds as the anchor at least doubles in size in the wound. It is most important to secure and add an extra mode of pressure that can help slow down or stop blood flow into the wound and out of the injured person. And this pressure is applied to the wound interior and exterior in a hands-free manner as the simple deployment of the anchors into the wound achieves these functions.

The number of anchors needed for a particular wound will depend upon the size and depth of the wound. In some situations, only the first or first and second anchors are sufficient to lose the wound. For deeper or wider wounds, additional anchors can be deployed. And once deployed, a dressing of a gauze or absorbable pad, can then be placed over the wound to assure that the anchors remain therein if the injured person is moved. The dressing can be provided secured to the patient using medical tape to further confine and retain the anchors in place.

Once the anchors are deployed in the wound, the tether 220 can be pulled to assure that anchors are securely embedded in position. Pulling the tether can cause the anchors to change shape to more effectively and fully block the wound. There are situations where all of the anchors are deployed into the wound although in many cases not all enter into the wound. These remain outside the wound where they can help to absorb residual blood as well as to provide a partial covering over the wound.

And as shown in FIGS. 7-9, at the rear end of the anchors, a dressing 225 is also provided. This is again a gauze or absorbable pad. It is secured to the anchors by the tether 220 and by a larger end component 225 that prevents passage of the rear end of the tether though the dressing and anchors. Preferably the rear end component 230 is an RFID tag. And after the device is deployed and effectively anchored, the tether can be grasped to push the wound dressing and any remaining external anchors on the exterior of the wound. As the device is removed the dressing slides down and compresses. The dressing slides one way towards the wound exterior on the tether until contact and slight pressure achieved. This will leave the dressing hands-free while still keeping pressure on both interior and exterior of wound. The hands-free feature is very important in both a tactical or emergency situation. Multiple injuries or multiple people can potentially be cared for due to this hands-free feature.

FIGS. 10-12 illustrate the anchors being deployed (FIG. 10), the expansion of the lead and second anchors (FIG. 12) and the placement of the anchors in the wound (FIG. 11). For ease of viewing, the tether and dressing are not shown in FIG. 11. The number of anchors connected by the tether can vary depending upon the size and shape of the anchors. For this embodiment, approximately 10 anchors are used. For a 1" deep wound, approximately 5 anchors are deployed to fill the wound, while for a 2" deep wound, all 10 anchors would be deployed and placed in the wound as shown.

Figure 15:
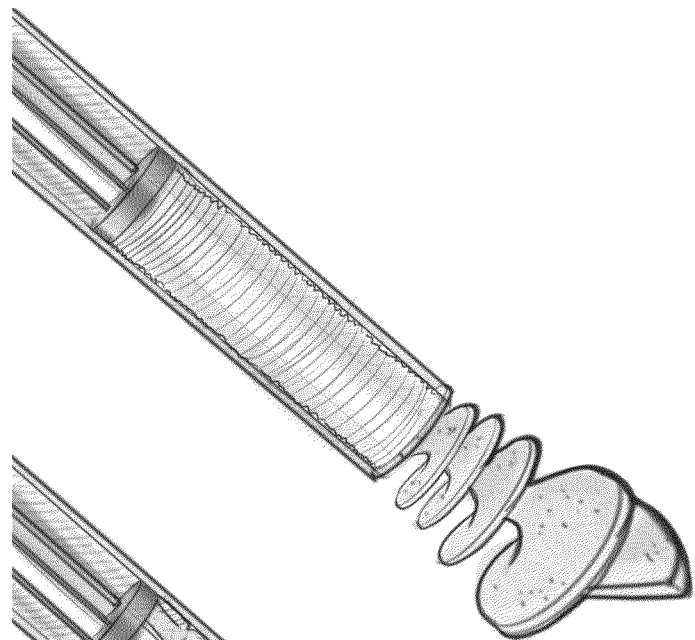
FIGS. 13-15 are views of different anchors that are being deployed from the device.
Figure 14:
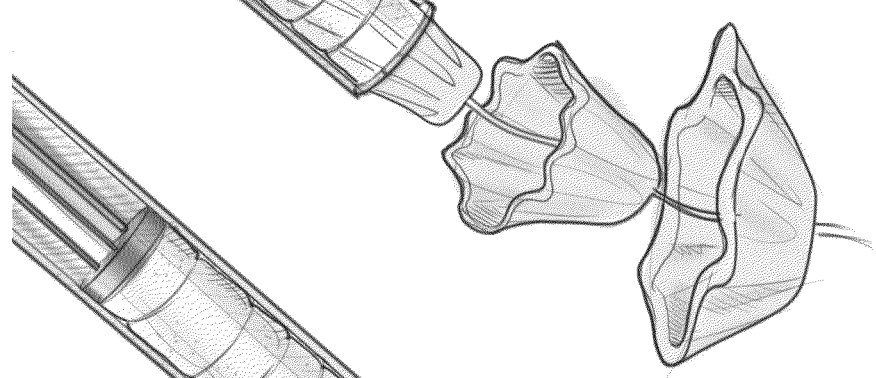
Figure 13:
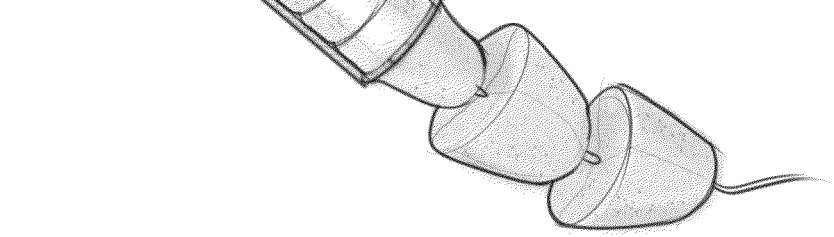

FIGS. 13 to 24 illustrate different types of anchors and related materials for deployment into the wound. FIG. 13 illustrates foam anchors, while FIG. 14 illustrates irregular shaped cup anchors. The latter are preferred for larger wounds since it is important to fill the wound as quick as possible to limit blood loss. FIG. 15 illustrates a screw or spiral shaped absorbent structure that can be deployed into an irregularly shaped wound.

Figure 21:
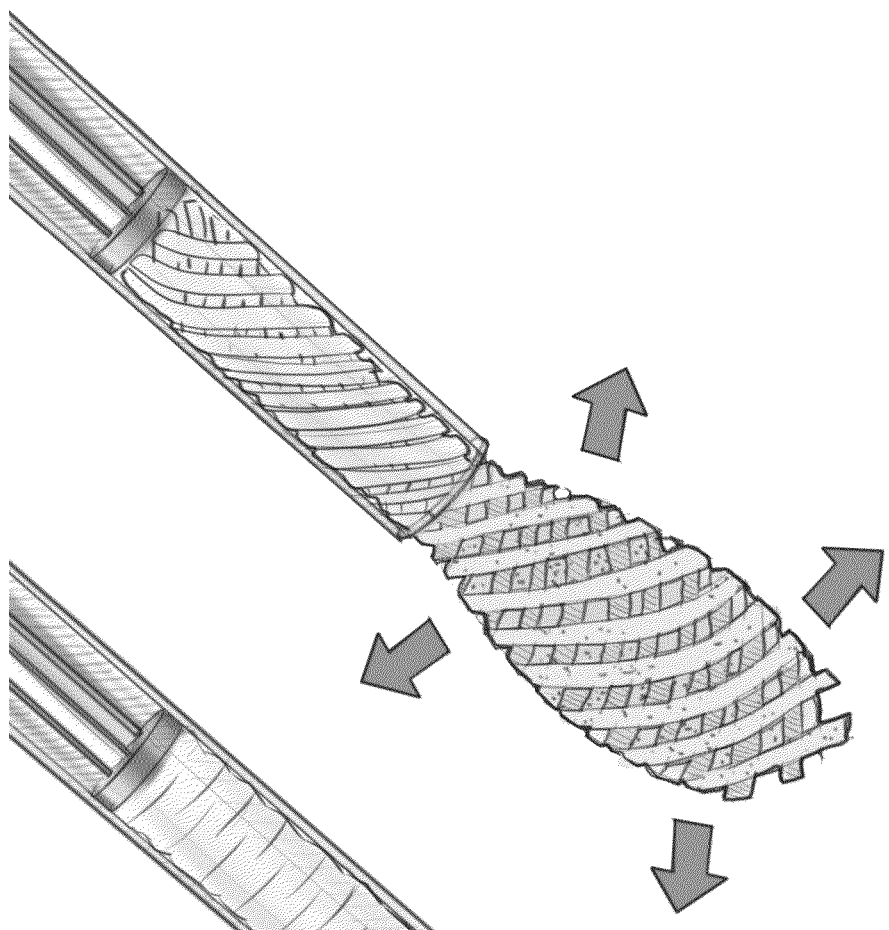
FIGS. 19-21 are views of additional, different anchors that are being deployed from the device.
Figure 20:
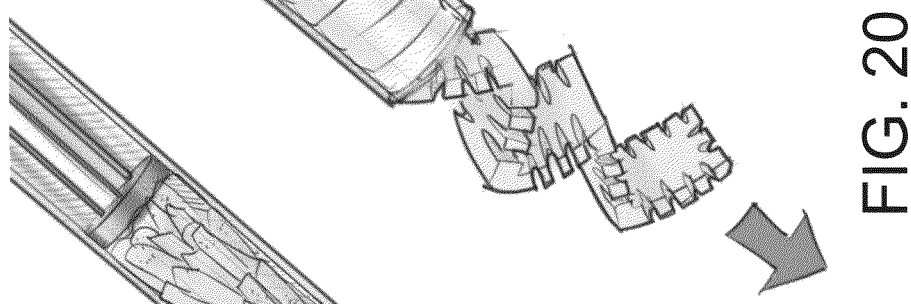
Figure 19:
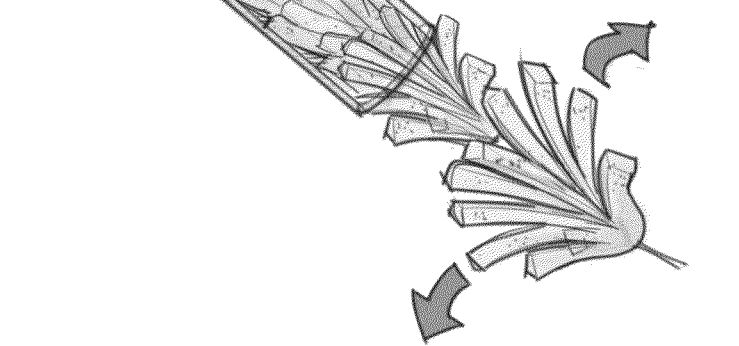
Figure 28:
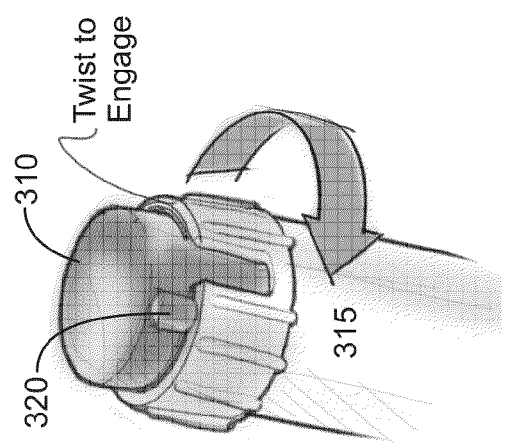
FIGS. 26-29 are views of a spring loaded device and a twist mechanism that is used to engage and activate the device.
Figure 29:
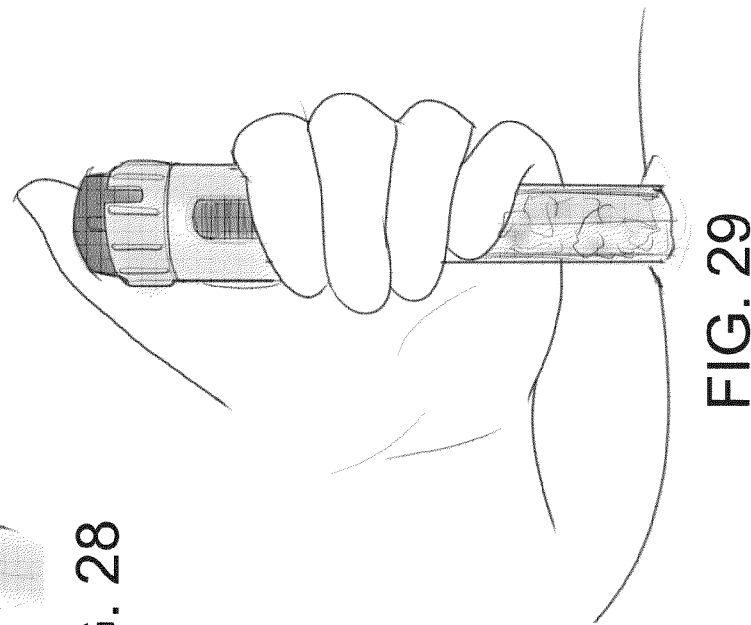
Figure 26:
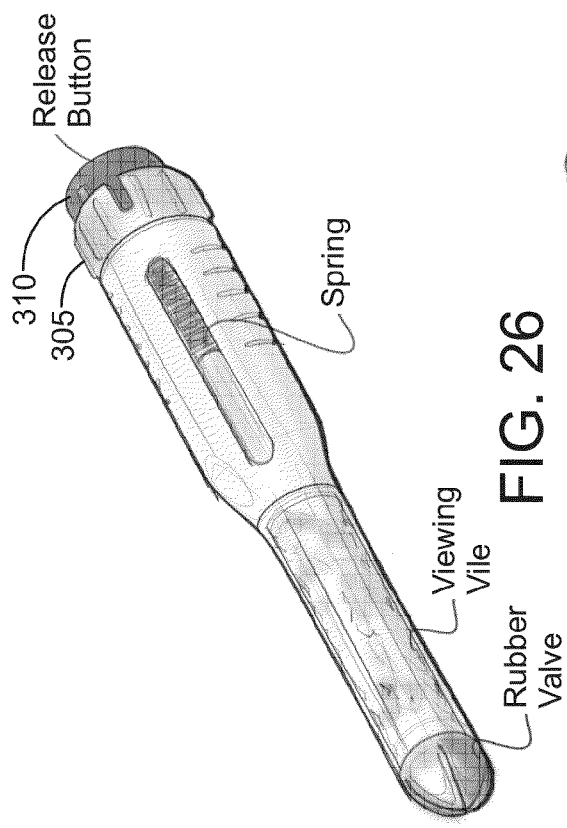
Figure 27:
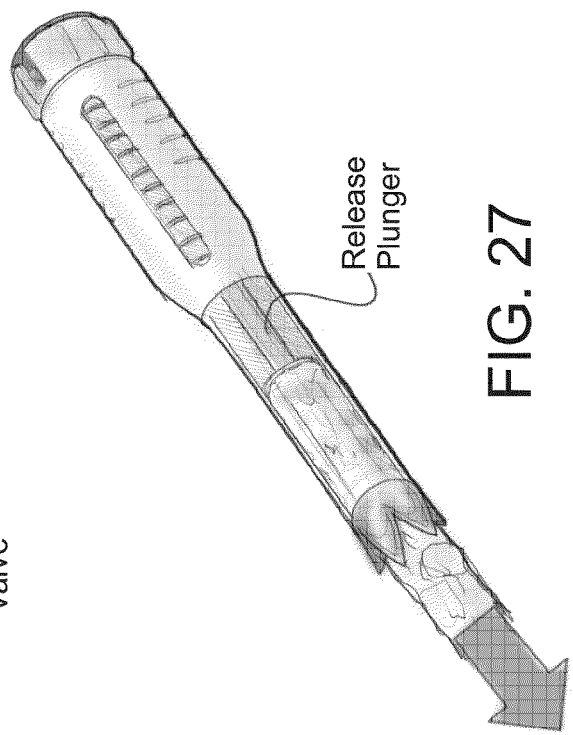

FIGS. 16 to 18 illustrate a plurality of strand shaped anchors that can be deployed into deep wounds. As shown in FIG. 16, the strands can be would around the piston or plunger to facilitate delivery of the strands into the wound. FIGS. 19-21 illustrate additional shapes of anchors that can be used in different wound situations.

FIGS. 22-23 illustrate a variation of the device when a single foam or gauze absorbent anchor is deployed. This is generally used for larger wounds. The forward end of the anchor would include the tether securely attached thereto and it would also expend out of the back end as shown.

FIGS. 24-25 illustrate the deployment of a liquid absorbent material that can be injected into the wound. The material would be one that would expand when in contact with blood and which would form a solid plug after setting up in the wound.

FIGS. 26-29 illustrate a modified device 300 that has a safety mechanism 305 supporting and operatively associated with the trigger 310. The safety mechanism 305 is a rotatable cylinder that is present at the rearward end of the device. The safety mechanism 305 includes slot 315 whereas trigger 310 include protrusion 320. The trigger 310 cannot be depressed until the slot 315 is aligned with the protrusion 320. When the device is to be activated, the user twists or rotates the safety mechanism in a counterclockwise direction to achieve alignment which would allow the trigger to be depressed. As in the other embodiments, this action can be conducted using one hand.

FIGS. 30-33 illustrate a similar arrangement except that the interfering components are present inside the upper housing. Again, the upper housing needs to be rotated or twisted in a counterclockwise direction in order to align the upper and lower portions of the body to allow the trigger button to be depressed to activate the device and deploy the anchors.

FIGS. 34-37 illustrate a second embodiment of the invention wherein the device is manually actuated. This manual device 400 includes a plunger 410 similar to that found in a conventional syringe. The manual device 400 will also have a distal cap and safety 420 that will keep the anchors sterile before use and that must be removed prior to use. The manual device 400 also include depth limiter 425. It will deploy the same types of anchors as the powered device. For example, anchors 200 are suitable for use in this device. Again, it is designed for one hand use to facilitate rapid deployment.

The manual device is intended to be used by trained or medical personnel preferably in a hospital, ambulance or medical clinic setting. This device is more cost effective than the powered device. It also has better tactical feedback.

Data from the RFID tag that is attached to the tether provided extremely accurate usage data points when paired with receivers. This data can be used for logistical purposes, also before, during and after an event where the system and devices are deployed. This will save significant monies in logistics and tracking. During a deployment event this data can be used to assess the situation even before or after arrival of additional personnel. It can track numbers, usage, GPS and any other features traceable with RFID and Blockchain technology. After a deployment event, this data can be used for forensics, education, training or product improvement. When a metal tether is used, it can act as an antenna to transmit RFID information. It also can be viewed by x-rays to be sure that the entire tether has been removed after the subject receives medical treatment in a hospital.

There is a general rule in surgery that unless a device was intended for implantation it must be removed prior to surgery completion. Multiple consequences and complications including death can and will occur if a foreign body is left in the body. With this device the anchors and tether are radiolucent and can be seen under X-ray, MRI and CT-scan. This should not be an issue because the tether completely attaches and secures all of the anchors and is used for removal. The anchors are designed to reverse the shape of the anchor when a significant force is applied opposite to the deployment force. This will allow for device removal when medically necessary. This will also significantly save time in surgery because of the easy removal and no loose bodies to find and remove. This feature should significantly improve survivability and infection rates post-operatively.

As with rules in surgery there are rules in tactical medicine. The earlier an EMT can intervene and provide definitive life-saving interventions the better chance of survival the patient will have. With more and more municipalities training their EMT's and Fire Departments in Tactical medicine, much like combat medics in the military, the need for a device like the WASP is increasing. The WASP will serve in addition to already employed life saving devices such as the tourniquet and pressure dressings but will fill an important void that those devices simply cannot affect. Specifically, torso and transitional areas of the body as well as wounds that do not require a tourniquet. Current training states that when in doubt in a chaotic situation apply a tourniquet, while in the short term this will stop the bleeding and save the life it may cause long term damage to the extremity, employing the WASP when arterial bleeding is not present will not only safely and effectively control any bleeding but will also prevent infection and preserve long term functionality of that limb. The WASP greatly increases survivability at the point of injury, expedites evacuation times, decreases infection rates, and revolutionizes point-of-injury treatment.

These devices can be a standalone product or part of a kit or system. When used in a kit, a clamshell container can be used to house the device itself, reloadable cartridges, and with various other wound products such as tourniquets, bandages, gloves, flashlight, medications, and general first aid devices to enhance or assist the device or multiple injuries. This device or the manual device can be prepositioned like an AED or fire extinguisher for visibility and viability in a situation. It can also be provided in a more compact housing that can be worn on a belt or carried in a pocket.

What is claimed is:

1. A device for filling a person's wound to stop bleeding therefrom, comprising:
a body comprising:
a lower section having an interior portion that stores at least one or a plurality of expandable anchor(s) made of blood absorbing material that expands in size initially after leaving the body and further upon contacting and absorbing blood;
an upper section having an interior portion that contains an expandable anchor deployment component configured to deploy the expandable anchor(s) from the lower section;
a forward end including a knife blade, and a depth limiter, wherein the knife blade is configured to cut through a skin surface to facilitate introduction of the forward end and deployment of the expandable anchor(s); and the depth limiter is configured to control insertion depth of the device into the person's wound, the depth limiter having a diameter larger than that of the lower section and the upper section, the depth limiter positioned between the knife blade and the lower section; and
a removable cap configured to cover the forward end, at least a portion of the removable cap having a diameter equal to the diameter of the depth limiter.

2. The device of claim 1, wherein the forward end further comprises a tip and a neck connecting the tip and the lower section, wherein the tip is configured to close off the interior portion of the lower section, the tip includes a plurality of slits through which the expandable anchor(s) pass when deployed with the slits configured to separate the expandable anchor(s) during multiple expandable anchor deployment.

3. The device of claim 2, wherein the knife blade is positioned on the neck and has a length between 1 and 4 mm.

4. The device of claim 1, wherein the depth limiter is part of the lower section and is the widest portion of the lower section with a width that is also larger than that of the forward end.

5. The device of claim 1, wherein the expandable anchor deployment component is a replaceable cartridge that contains carbon dioxide and a piston that is moved to deploy the expandable anchor(s) when carbon dioxide is released from the cartridge.

6. The device of claim 5, wherein the body further comprises:
a trigger button configured to deploy the expandable anchor(s) from the interior portion of the lower section through the forward end by releasing carbon dioxide from the cartridge; and
a safety switch on the body configured to prevent the trigger button from deploying the expandable anchor(s) until desired.

7. The device of claim 6, wherein the safety switch is positioned along a side of the upper section and the trigger button is positioned at a free end of the upper section.

8. The device of claim 1, wherein the upper section includes multiple non-slip rubber grips for handling.

9. The device of claim 1, wherein the expandable anchor(s) have a first size while being stored in the interior portion of the lower section and a second size after being deployed from the device, the second size is larger than the first size resulting from initial expansion of the expandable anchor(s) after deployment from the interior portion of the lower section.

10. The device of claim 9, wherein multiple expandable anchors are present and are joined together by a tether penetrating through each of the expandable anchors, with the expandable anchors made of cotton, polymers, or a combination thereof and optionally including hemostatic agents, antibiotics, medicines, or a combination thereof.

11. The device of claim 1, wherein the expandable anchor deployment component is a plunger that is movable within the upper section to deploy the expandable anchor(s) through the forward end of the device.

12. The device of claim 1, wherein the forward end further comprises a neck extending from the depth limiter and configured to be inserted into the person's wound.

13. The device of claim 12, wherein the neck has a diameter smaller than that of the upper section.

14. The device of claim 1, wherein the expandable anchor deployment component comprises:
a trigger button coupled to a rear end of the body opposite the forward end, the trigger button configured to deploy the expandable anchor(s) from the interior portion of the lower section through the forward end; and
a safety switch coupled to the upper section closer to the rear end than to the forward end, the safety switch configured to prevent the trigger button from deploying the expandable anchor(s) until actuated.

* * * * *